(12) United States Patent  (10) Patent No.: US 8,093,242 B2
Anderton et al.  (45) Date of Patent: Jan. 10, 2012

(54) CRYSTALLINE FORMS OF A PYRIDINE DERIVATIVE

(75) Inventors: Clare Louise Anderton, Stevenage (GB); Ronnie Maxwell Lawrence, Stevenage (GB); David Clapham, Ware (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/056,775

(22) PCT Filed: Aug. 4, 2009

(86) PCT No.: PCT/EP2009/060089
§ 371 (c)(1),
(2), (4) Date: Jan. 31, 2001

(87) PCT Pub. No.: WO2010/015626
PCT Pub. Date: Feb. 11, 2010

(65) Prior Publication Data
US 2011/0136798 A1   Jun. 9, 2011

(30) Foreign Application Priority Data
Aug. 5, 2008  (GB) .................................. 0814340.6

(51) Int. Cl.
*C07D 498/04* (2006.01)
*A61K 31/4985* (2006.01)
(52) U.S. Cl. ...................................... 514/230.5; 544/105
(58) Field of Classification Search .................. 544/105; 514/230.5
See application file for complete search history.

(56) References Cited

U.S. PATENT DOCUMENTS

| 7,005,436 | B2 | 2/2006 | Lloyd et al. | |
|---|---|---|---|---|
| 7,582,654 | B2 | 9/2009 | Lloyd et al. | |
| 7,683,056 | B2 * | 3/2010 | Alvaro et al. | 514/230.5 |
| 2005/0090533 | A1 | 4/2005 | Hoffmann | |

FOREIGN PATENT DOCUMENTS

| EP | 1035115 B1 | 9/2000 |
|---|---|---|
| WO | 9802158 | 1/1998 |
| WO | 0130348 | 5/2001 |
| WO | 03066621 A1 | 8/2003 |
| WO | 03066635 A | 8/2003 |
| WO | 2005002577 A | 1/2005 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Ikeura, Y., et al.; Potent NK1 Receptor Antagonists: Synthesis and Antagonistic Activity of various Heterocycles with anN-[3,5-Bis(trifluoremethyl)benzyl]-N-methylcarbamoyl Substituent; Chem. Pharm. Bull.; 1997; 45/10; 1642-1652; Pharmaceutical Society of Japan.
Challet, E., et al.; The Selective neurokinin 1 Receptor Antagonist R116301 Modulates Photic Responses of the Hamster Circadian System; Neuropharmacology; 2001; 40; 408-415.
Natsugari, H. et al.; Novel, Potent and orally active substance P Antagonists: Synthesis and Antagonist Activity of N-Benzylcarboxamide Derivatives of Pyrido [3,4-b] pyridine; Journal Medical Chemistry; 1995; 38; 3106-3120; American Chemical Society.
George, D.T., et al.; Neurokinin 1 Receptor Antagonist As Possible Therapy for Alcoholism; Science; 2008; 319; 1536-1539.
Ciccocioppo, R., et al.; Selective Antagonist At NK3 Tachykinin Receptors Inhibit Alcohol Intake in Sardinian Alcohol-Preferring Rats; Brain Research Bulletin; 1994; 33(1); 71-77.
Substance-Related Disorders; Diagnostic and Statistical Manual of Mental Disorders; 4th Edith, Text Revision; 191-197; American Psychiatric Association, (2000).
Challet, E., et al.; An NK1 Receptor Antagonist Affects the Circadian Regulation of Locomotor Activity in Golden Hamsters; Brain Research; 1998; 800; 32-39.

* cited by examiner

*Primary Examiner* — Kahsay T Habte
(74) *Attorney, Agent, or Firm* — J. Scott Young

(57) ABSTRACT

The invention relates to 4-methylbenzenesulfonate salt of the compound of formula (I)

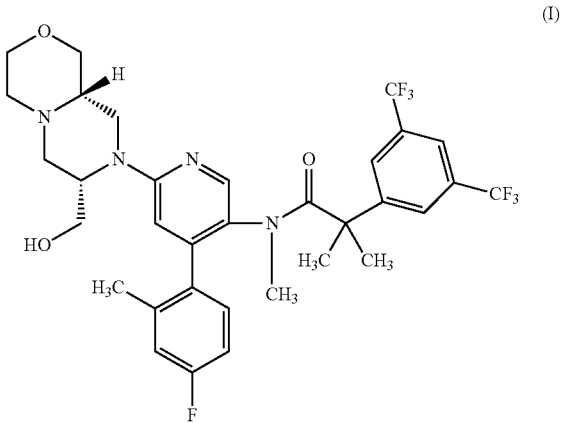

in a crystalline form or a solvate thereof, pharmaceutical formulations containing them, their use in therapy and processes for preparing the same.

9 Claims, 6 Drawing Sheets

Intensity (counts)

Figure 1 – XRPD pattern of 4-methylbenzenesulfonate salt of the compound of formula (I) anhydrous crystalline Form 1

Figure 2- DSC for 4-methylbenzenesulfonate salt of the compound of formula (I) anhydrous crystalline Form 1

Figure 3 – XRPD pattern of 4-methylbenzenesulfonate salt of the compound of formula (I) anhydrous crystalline Form 2

Figure 4 - DSC for 4-methylbenzenesulfonate salt of the compound of formula (I) anhydrous crystalline Form 2

Figure 5-XRPD pattern of 4-methylbenzenesulfonate salt of the compound of formula (I) in a hydrate crystalline form (hydrate 1)

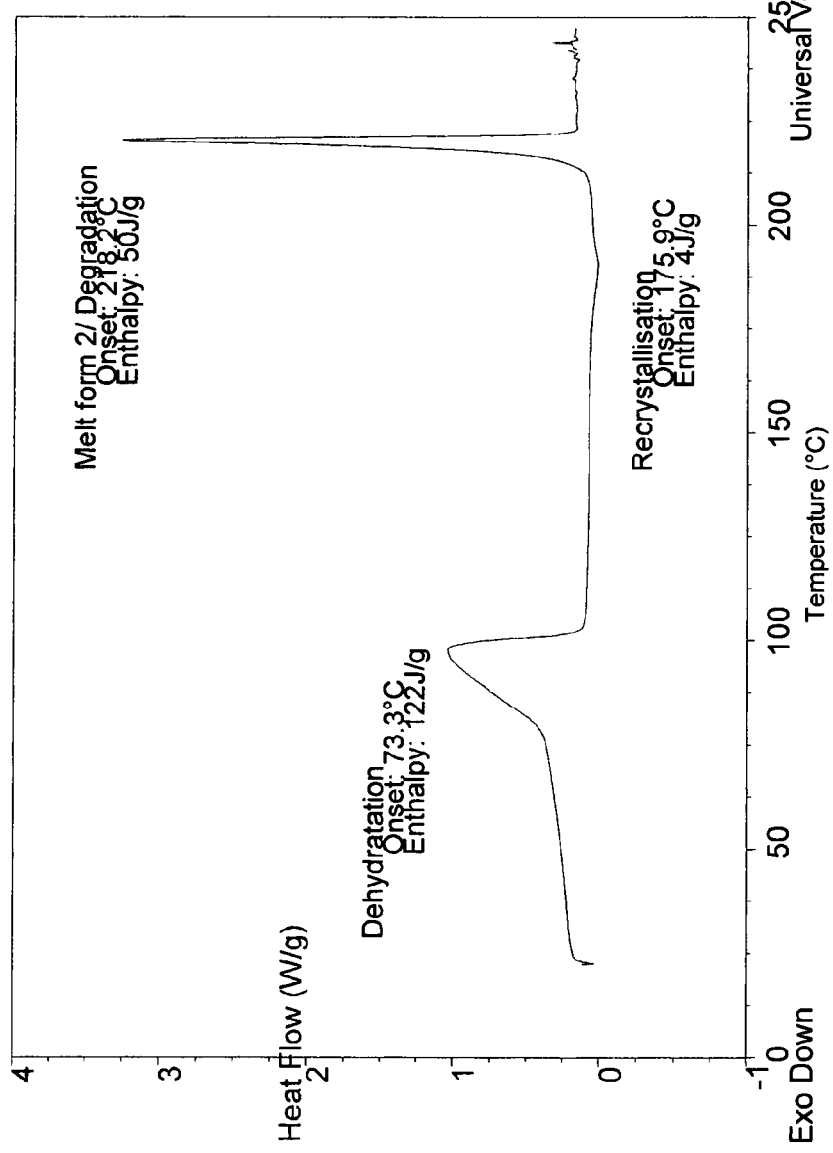
Figure 6 – DSC for 4-methylbenzenesulfonate salt of the compound of formula (I) in a hydrate crystalline form (hydrate 1)

CRYSTALLINE FORMS OF A PYRIDINE DERIVATIVE

CROSS-REFERENCE TO RELATED APPLICATIONS

This application is filed pursuant to 35 USC 371 as a United States National Phase Application of International Patent Application Serial No. PCT/EP2009/060089 filed on Aug. 4, 2009, which claims priority from 0814340.6 filed on Aug. 5, 2008 in the United Kingdom.

FIELD OF THE INVENTION

The present invention relates to crystalline forms of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide 4-methylbenzenesulfonate or a solvate thereof, pharmaceutical formulations containing them, their use in therapy and processes for preparing the same. This compound is an antagonist of the NK1 and NK3 receptor and thus may be of use in the treatment of psychotic disorders, depression, mood disorders, anxiety, sleep disorders and substance-related disorders.

BACKGROUND OF THE INVENTION

WO07/028654 describes a number of pyridine derivatives or pharmaceutical acceptable salts thereof as antagonists of the NK1 and NK3 receptor and thus may be of use in the treatment of psychotic disorders. In particular, the compound 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide or pharmaceutical acceptable salts thereof are described in this application.

Hydrochloride salt of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide is also described in WO07/028654.

The structure of the 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide is shown in formula (I) below.

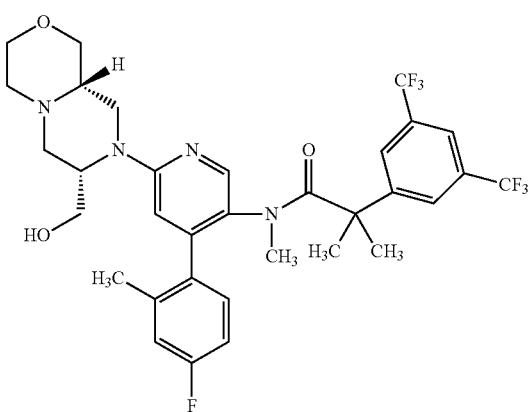

(I)

Pharmaceutical acceptable salts of the compound of formula (I) include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

The compound of formula (I) as free base or as hydrochloride is obtained, according to the procedure described in WO07/028654 or in the present application, as partially amorphous or wholly amorphous solids and it is hygroscopic. Amorphous solids and particularly hygroscopic solids are difficult to handle under pharmaceutical processing conditions because of low typically bulky densities and unsatisfactory flow properties.

Accordingly, a need exists for crystalline forms of the compound of formula (I) with superior physiochemical properties that may be used advantageously in pharmaceutical processing and pharmaceutical compositions.

SUMMARY OF THE INVENTION

We have now found that the 4-methylbenzenesulfonate salt (also known as tosylate or p-toluenesulfonate salt) of the compound of formula (I) or a solvate thereof can be obtained in a crystalline form and it exhibits polymorphism.

In a first aspect of the invention, there is provided 4-methylbenzenesulfonate salt of the compound of formula (I) or a solvate thereof in a crystalline form.

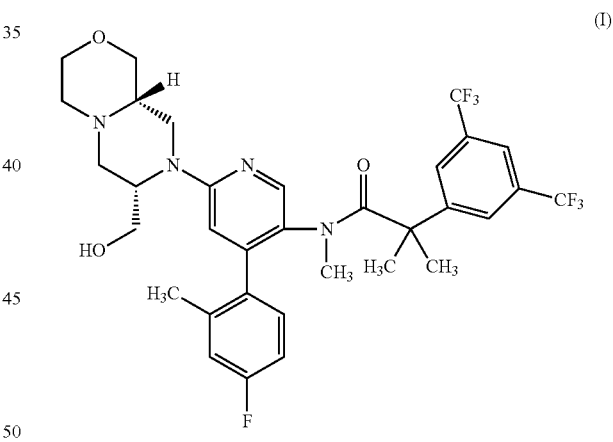

(I)

In a second aspect of the invention, there is provided 4-methylbenzenesulfonate salt of the compound of formula (I) in a crystalline form.

In a third aspect of the present invention, there is provided 4-methylbenzenesulfonate salt of the compound of formula (I) in an anhydrous crystalline form.

In a fourth aspect of the present invention, there is provided 4-methylbenzenesulfonate salt of the compound of formula (I) in anhydrous crystalline Form 1, wherein the XRPD pattern is expressed in terms of 2 theta angles and obtained with a diffractometer equipped with a diffracted beam graphite monochromator using copper Kα X-radiation.

In a fifth aspect of the present invention, there is provided 4-methylbenzenesulfonate salt of the compound of formula (I) in anhydrous crystalline Form 1 characterized by substantially the same X-ray powder diffraction (XRPD) pattern as in FIG. 1, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 8.0±0.1, 10.3±0.1, 14.5±0.1, 15.0±0.1, 17.7±0.1 degrees, which correspond respectively to d-spacing at 11.0, 8.6, 6.1, 5.9 and 5.0 Angstroms (Å).

In a sixth aspect of the present invention, there is provided 4-methylbenzenesulfonate salt of the compound of formula (I) in anhydrous crystalline Form 1 characterized by substantially the same X-ray powder diffraction (XRPD) pattern as in FIG. 1, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 3.2±0.1, 6.2±0.1, 8.0±0.1, 10.3±0.1, 12.4±0.1, 14.5±0.1, 15.0±0.1, 16.2±0.1, 17.2±0.1, 17.7±0.1, 18.6±0.1, 20.0±0.1, 22.9±0.1 degrees, which correspond respectively to d-spacings at 28.0, 14.2, 11.0, 8.6, 7.1, 6.1, 5.9, 5.5, 5.2, 5.0, 4.8, 4.4 and 3.9 Angstroms (Å).

In a seventh aspect of the present invention, there is provided 4-methylbenzenesulfonate salt of the compound of formula (I) in anhydrous crystalline Form 2 characterized by substantially the same X-ray powder diffraction (XRPD) pattern as in FIG. 3, wherein the XRPD pattern is expressed in terms of 2 theta angles and obtained with a diffractometer equipped with a diffracted beam graphite monochromator using copper Kα X-radiation.

In an eighth aspect of the present invention, there is provided 4-methylbenzenesulfonate salt of the compound of formula (I) in anhydrous crystalline Form 2 characterized by substantially the same X-ray powder diffraction (XRPD) pattern as in FIG. 3, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 8.3±0.1, 9.3±0.1, 10.2±0.1, 11.2±0.1, 13.6±0.1 degrees, which correspond respectively to d-spacing at 10.7, 9.5, 8.7, 7.9 and 6.5 Angstroms (Å).

In a ninth aspect of the present invention, there is provided 4-methylbenzenesulfonate salt of the compound of formula (I) in anhydrous crystalline Form 2 characterized by substantially the same X-ray powder diffraction (XRPD) pattern as FIG. 3, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 3.2±0.1, 6.3±0.1, 8.3±0.1, 9.3±0.1, 10.2±0.1, 11.2±0.1, 12.3±0.1, 13.6±0.1, 15.6±0.1, 16.2±0.1, 16.4±0.1, 17.2±0.1, 20.4±0.1, 22.4±0.1, 27.3±0.1, 28.5±0.1 degrees, which correspond respectively to d-spacings at 27.8, 14.1, 10.7, 9.5, 8.7, 7.9, 7.2, 6.5, 5.7, 5.5, 5.4, 5.1, 4.4, 4.0, 3.3 and 3.1 Angstroms (Å).

In a tenth aspect of the present invention, there is provided 4-methylbenzenesulfonate salt of the compound of formula (I) in a hydrate crystalline form.

In an eleventh aspect of the present invention, there is provided 4-methylbenzenesulfonate salt of the compound of formula (I) in hydrate crystalline form (hydrate1) characterized by substantially the same X-ray powder diffraction (XRPD) pattern as in FIG. 5, wherein the XRPD pattern is expressed in terms of 2 theta angles and obtained with a diffractometer equipped with a diffracted beam graphite monochromator using copper Kα X-radiation.

In a twelfth aspect of the present invention, there is provided 4-methylbenzenesulfonate salt of the compound of formula (I) in hydrate crystalline form (hydrate 1) characterized by substantially the same X-ray powder diffraction (XRPD) pattern as in FIG. 5, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 7.8±0.1, 10.4±0.1, 12.1±0.1, 13.1±0.1, 18.3±0.1 degrees, which correspond respectively to d-spacing at 11.3, 8.5, 7.3, 6.8 and 4.9 Angstroms (Å).

In a thirteenth aspect of the present invention, there is provided 4-methylbenzenesulfonate salt of the compound of formula (I) in hydrate crystalline form (hydrate 1) characterized by substantially the same X-ray powder diffraction (XRPD) pattern as in FIG. 5, wherein the XRPD pattern is expressed in terms of 2 theta angles and obtained with a diffractometer equipped with a diffracted beam graphite monochromator using copper Kα X-radiation, wherein the XRPD pattern comprises 2 theta angle peaks at essentially the following positions: 7.8±0.1, 9.2±0.1, 10.4±0.1, 12.1±0.1, 13.1±0.1, 15.1±0.1, 15.6±0.1, 15.8±0.1, 18.3±0.1, 18.5±0.1, 19.4±0.1, 20.4±0.1, 21.2±0.1, 22.4±0.1, 22.7±0.1, 26.2±0.1 degrees, which correspond respectively to d-spacings at 11.3, 9.7, 8.5, 7.3, 6.8, 5.9, 5.7, 5.6, 4.9, 4.8, 4.6, 4.4, 4.2, 4.0, 3.9, and 3.4 Angstroms (Å).

As another aspect, the present invention provides a pharmaceutical composition comprising 4-methylbenzenesulfonate salt of the compound of formula (I) or a solvate thereof in a crystalline form according to the present invention. The pharmaceutical composition may further comprise one or more pharmaceutically acceptable carriers or diluents.

As another aspect, the present invention provides a method for the treatment or prophylaxis of psychotic disorders, depression, mood disorders, anxiety, sleep disorders and substance-related disorders comprising administering to the mammal, an effective amount of 4-methylbenzenesulfonate salt of the compound of formula (I) or a solvate thereof in a crystalline form according to the present invention.

As another aspect, the present invention provides 4-methylbenzenesulfonate salt of the compound of formula (I) or a solvate thereof in a crystalline form according to the present invention for use in therapy.

As another aspect, the present invention provides the use of 4-methylbenzenesulfonate salt of the compound of formula (I) or a solvate thereof in a crystalline form according to the present invention in the preparation of a medicament for the treatment or prophylaxis of psychotic disorders, depression, mood disorders, anxiety, sleep disorders and substance-related disorders.

BRIEF DESCRIPTION OF THE DRAWINGS

FIG. 6 depicts a differential scanning calorimetry (DSC) thermogram of 4-methylbenzenesulfonate salt of the compound of formula (I) in a hydrate crystalline form (hydrate 1). The DSC was carried out on a TA Q1000 TA system at a scan rate of 10° C. per minute, using a sample size of between 1 and 2 mg according to the procedures described herein.

DETAILED DESCRIPTION OF THE INVENTION

Figure 1:
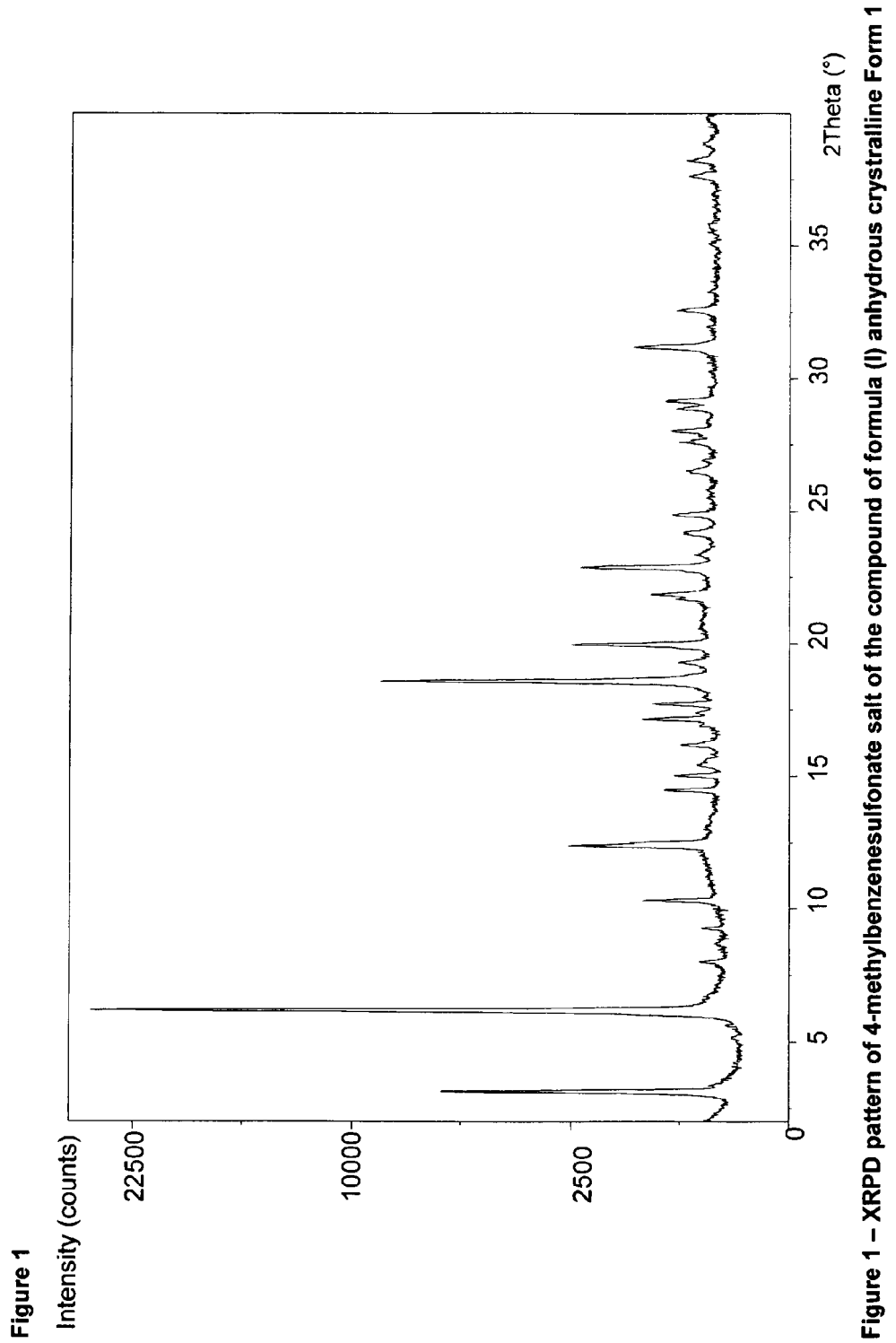
FIG. 1 depicts an X-ray powder diffraction (XRPD) pattern of 4-methylbenzenesulfonate salt of the compound of formula (I) anhydrous crystalline Form 1 according to the present invention. The XRPD pattern is expressed in terms of 2 theta angles and obtained with a diffractometer using copper Kα X-radiation, according to the procedures described herein.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "pharmaceutically acceptable salts" means those salts which are non-toxic and that are suitable for manufacturing and formulation as a pharmaceutical entity.

As used herein, the term "substantially the same X-ray powder diffraction pattern" is understood to mean that those X-ray powder diffraction patterns having diffraction peaks with 2 theta values within plus or minus 0.1° of the diffraction pattern referred to herein are within the scope of the referred to diffraction pattern. In a like manner, the term "at least substantially includes peaks of Table X" (where X is one of Tables I-III) is understood to mean that those X-ray powder diffraction patterns having diffraction peaks with 2 theta values within plus or minus 0.1° of the subject Table are within the scope of the diffraction pattern referenced to the Table X.

As used herein, the term "solvate" refers to a complex of variable stoichiometry formed by a solute (in this invention, 4-methylbenzenesulfonate salt of the compound of formula (I)) and a solvent. Those skilled in the art of organic chemistry will appreciate that many organic compounds can form such complexes with solvents in which they are reacted or from which they are precipitated or crystallized. Examples of suitable solvents include, but are not limited to, water, dioxane, 1-propanol, methanol, ethanol and acetone, toluene and tetrahydrofuran. Preferably, the solvent used is a pharmaceutically acceptable solvent. Examples of suitable pharmaceutically acceptable solvents include, without limitation, water, ethanol. Most preferably the solvent used is water. Where the solvent used is water such a solvate is referred to as a hydrate.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes: Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term depression and mood disorders includes Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

The term anxiety includes Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

The term sleep disorders includes primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The term substance related disorders includes Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

We have now found that the 4-methylbenzenesulfonate salt (also known as tosylate or p-toluene sulfonate salt) of the compound of formula (I) or a solvate thereof can be obtained in a crystalline form which surprisingly has particularly good pharmaceutical properties.

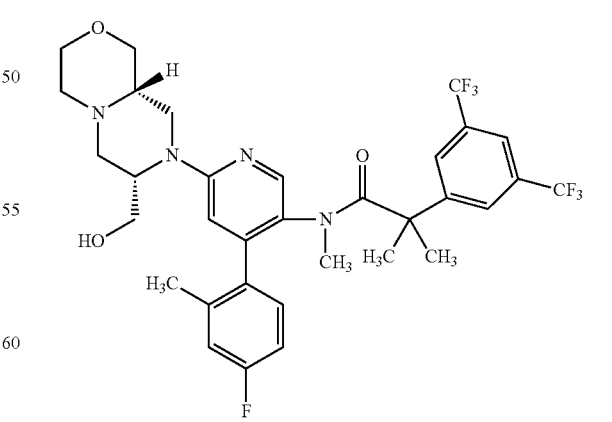

(I)

The wedge shaped bond indicates that the bond is above the plane of the paper. The broken bond indicates that the bond is below the plane of the paper.

Batches of a crystalline form can, by the processes of this invention, be made consistently to a high crystal form purity i.e., where the proportion of hydrated and other crystalline forms of 4-methylbenzenesulfonate salt of the compound of formula (I) is limited (particularly less than 20%).

The various polymorphic forms of 4-methylbenzenesulfonate salt of the compound of formula (I) may be characterized and differentiated using a number of conventional analytical techniques, including but not limited to X-ray powder diffraction (XRPD) and differential scanning calorimetry (DSC).

Polymorphism is defined as the ability of an element or compound to crystallise in more than one distinct crystalline phase. Thus, polymorphs are distinct solids sharing the same molecular formula, however since the properties of any solid depends on its structure, different polymorphs may exhibit distinct physical properties such as different solubility profiles, different melting points, different dissolution profiles, different thermal and/or photostability, different shelf life, different suspension properties and different physiological absorption rate. Inclusion of a solvent in the crystalline solid leads to solvates, and in the case of water as a solvent, hydrates.

Thus, the present invention provides 4-methylbenzenesulfonate salt of the compound of formula (I) or a solvate thereof in a crystalline form.

Depending on the solvent from which the 4-methylbenzenesulfonate salt is recovered, this may be obtained as a solvate and such a solvate also forms one aspect of the present invention. The solvate may be a pharmaceutically acceptable solvate. Suitable solvates includes hydrates.

Suitable solvents useful to prepare solvates include, but are not limited to, water, dioxane, 1-propanol, methanol, trifluoroethanol, acetone, toluene, and tetrahydrofuran. As it will be apparent to those skilled in the art, said solvents may also be useful as mixtures or in mixture with water.

In one embodiment, the crystalline form of 4-methylbenzenesulfonate salt of the compound of formula (I) is anhydrous.

In one embodiment, the anhydrous crystalline form of 4-methylbenzenesulfonate salt of the compound of formula (I) is Form 1.

In another embodiment, 4-methylbenzenesulfonate salt of the compound of formula (I) in anhydrous crystalline Form 1 is characterized by substantially the same X-ray powder diffraction (XRPD) pattern as in FIG. 1, wherein the XRPD pattern is expressed in terms of 2 theta angles and obtained with a diffractometer equipped with a diffracted beam graphite monochromator using copper Kα X-radiation.

Figure 2:
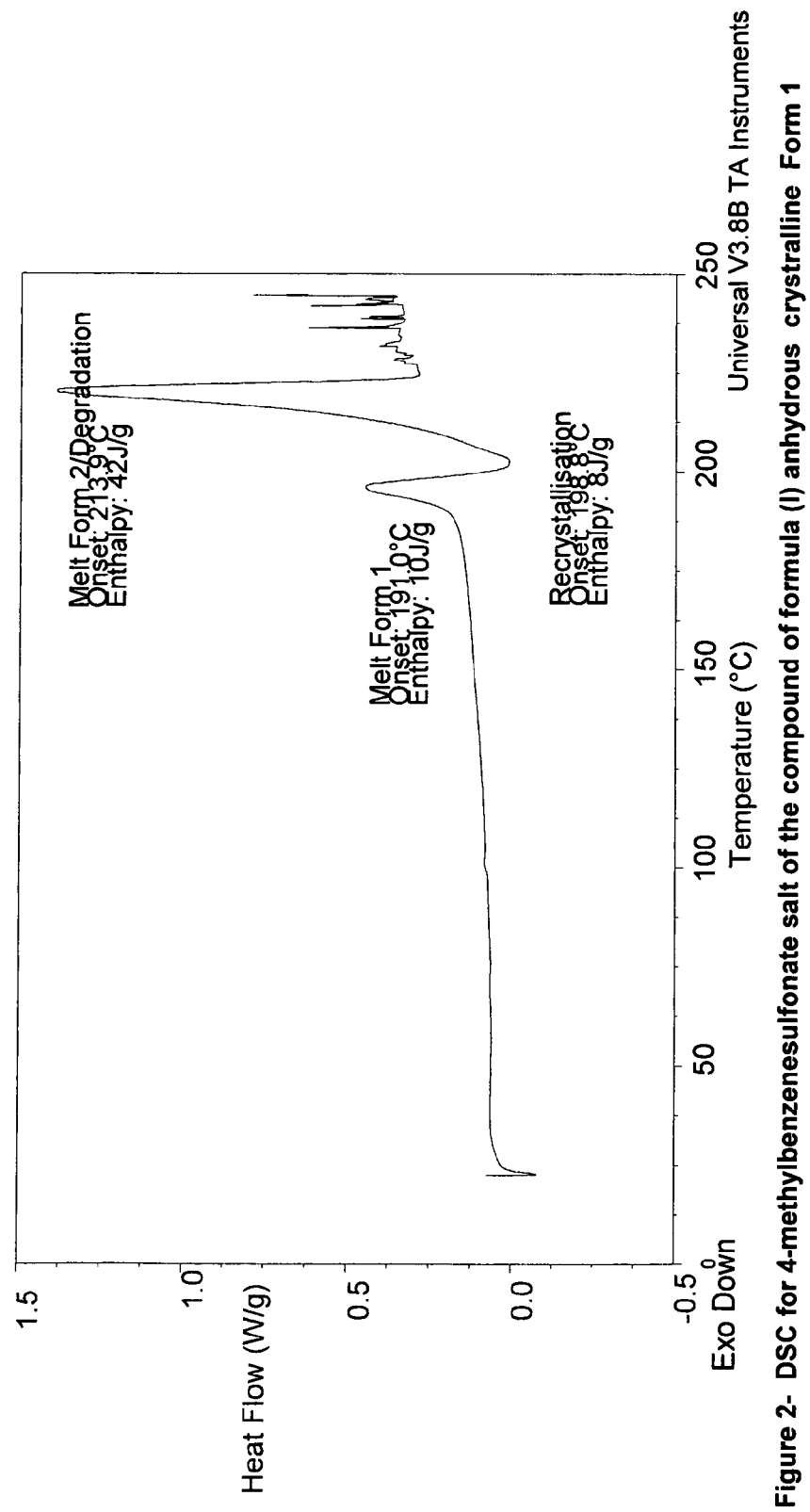
FIG. 2 depicts a differential scanning calorimetry (DSC) thermogram of 4-methylbenzenesulfonate salt of the compound of formula (I) anhydrous crystalline Form 1. The DSC was carried out on a TA Q1000 TA system at a scan rate of 10° C. per minute, using a sample size of between 1 and 2 mg according to the procedures described herein.

In another embodiment, 4-methylbenzenesulfonate salt of the compound of formula (I) in anhydrous crystalline Form 1 is characterized by substantially the same differential scanning calorimetry (DSC) thermogram shown in FIG. 2.

In another embodiment, 4-methylbenzenesulfonate salt of the compound of formula (I) in anhydrous crystalline Form 1 is characterized by an X-ray powder diffraction pattern which at least substantially includes the peaks of Table I.

TABLE I

| 2 theta angle (°)[1] | Å |
|---|---|
| 3.2 | 28.0 |
| 6.2 | 14.2 |
| 8.0 | 11.0 |
| 10.3 | 8.6 |
| 12.4 | 7.1 |

TABLE I-continued

| 2 theta angle (°)[1] | Å |
|---|---|
| 14.5 | 6.1 |
| 15.0 | 5.9 |
| 16.2 | 5.5 |
| 17.2 | 5.2 |
| 17.7 | 5.0 |
| 18.6 | 4.8 |
| 20.0 | 4.4 |
| 22.9 | 3.9 |

[1]Margin of error = approx. ±0.1 degrees.

In another embodiment, 4-methylbenzenesulfonate salt of the compound of formula (I) in anhydrous crystalline Form 1 is characterized by an X-ray powder diffraction pattern which at least substantially includes the X-ray powder diffraction (XRPD) °2θ peaks at essentially the following positions: 8.0±0.1, 10.3±0.1, 14.5±0.1, 15.0±0.1, 17.7±0.1 degrees, which correspond respectively to d-spacing at 11.0, 8.6, 6.1, 5.9 and 5.0 Angstroms (Å).

In another embodiment, the anhydrous crystalline form of 4-methylbenzenesulfonate salt of the compound of formula (I) is Form 2.

Figure 3:
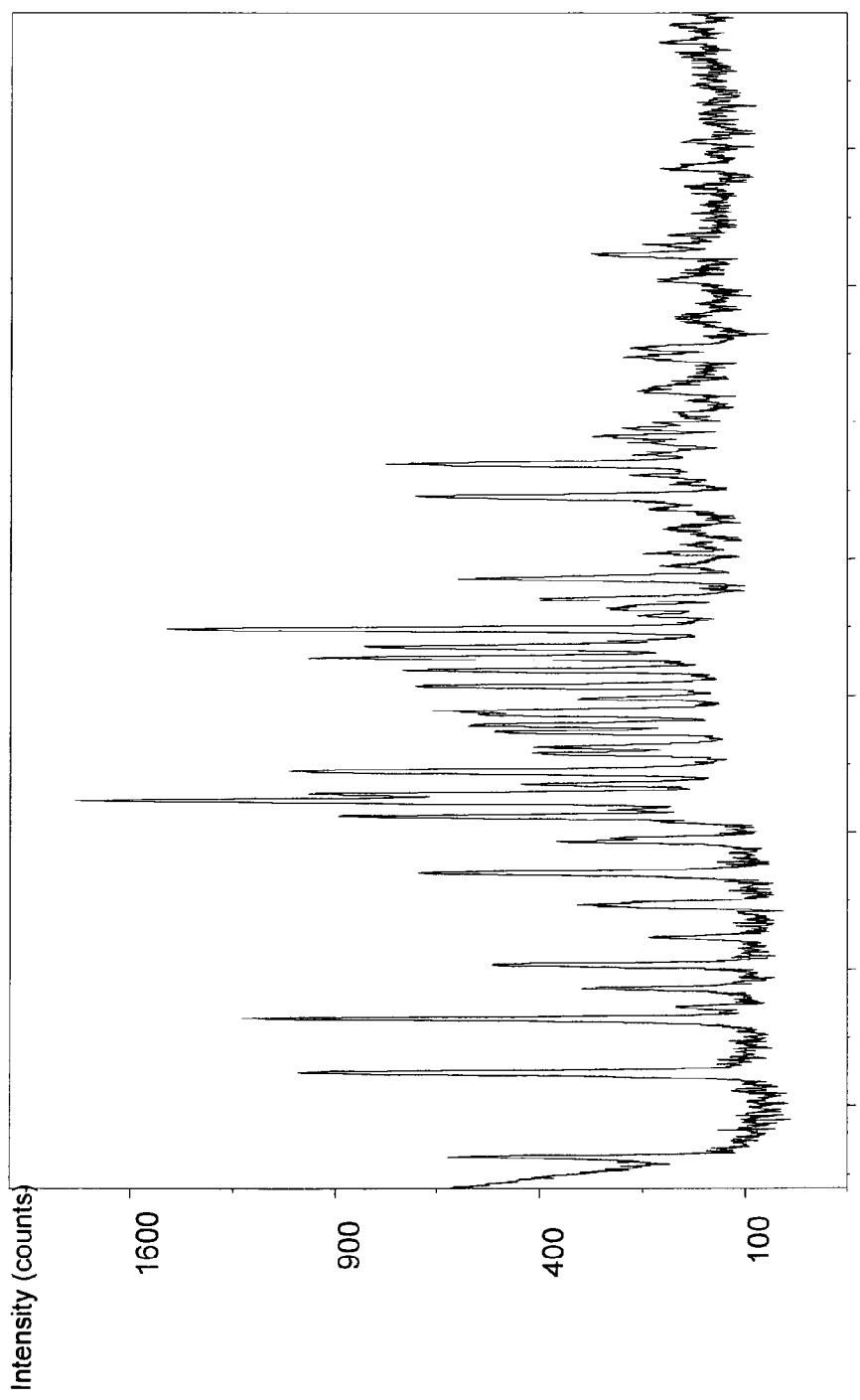
FIG. 3 depicts an X-ray powder diffraction (XRPD) pattern of 4-methylbenzenesulfonate salt of the compound of formula (I) anhydrous crystalline Form 2 according to the present invention. The XRPD pattern is expressed in terms of 2 theta angles and obtained with a diffractometer using copper Kα X-radiation, according to the procedures described herein.

In another embodiment, 4-methylbenzenesulfonate salt of the compound of formula (I) in anhydrous crystalline Form 2 is characterized by substantially the same X-ray powder diffraction (XRPD) pattern as in FIG. 3, wherein the XRPD pattern is expressed in terms of 2 theta angles and obtained with a diffractometer equipped with a diffracted beam graphite monochromator using copper Kα X-radiation.

Figure 4:
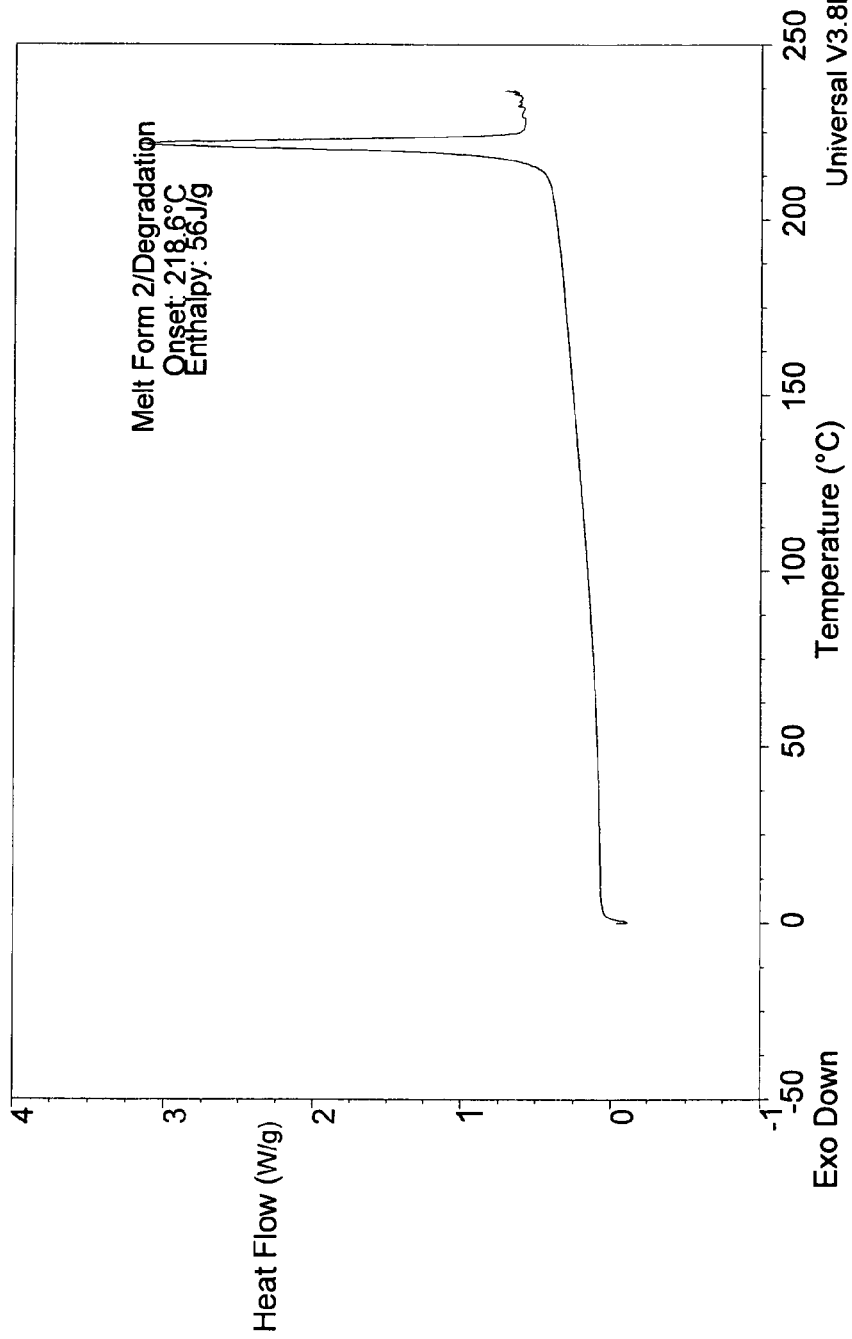
FIG. 4 depicts a differential scanning calorimetry (DSC) thermogram of 4-methylbenzenesulfonate salt of the compound of formula (I) anhydrous crystalline Form 2. The DSC was carried out on a TA Q1000 TA system at a scan rate of 10° C. per minute, using a sample size of between 1 and 2 mg according to the procedures described herein.

In another embodiment, 4-methylbenzenesulfonate salt of the compound of formula (I) in anhydrous crystalline Form 2 is characterized by substantially the same differential scanning calorimetry (DSC) thermogram shown in FIG. 4.

In another embodiment, 4-methylbenzenesulfonate salt of the compound of formula (I) in anhydrous crystalline Form 2 is characterized by an X-ray powder diffraction pattern which at least substantially includes the peaks of Table II.

TABLE II

| 2 theta angle (°)[1] | Å |
|---|---|
| 3.2 | 27.8 |
| 6.3 | 14.1 |
| 8.3 | 10.7 |
| 9.3 | 9.5 |
| 10.2 | 8.7 |
| 11.2 | 7.9 |
| 12.3 | 7.2 |
| 13.6 | 6.5 |
| 15.6 | 5.7 |
| 16.2 | 5.5 |
| 16.4 | 5.4 |
| 17.2 | 5.1 |
| 20.4 | 4.4 |
| 22.4 | 4.0 |
| 27.3 | 3.3 |
| 28.5 | 3.1 |

[1]Margin of error = approx. ±0.1 degrees.

In another embodiment, 4-methylbenzenesulfonate salt of the compound of formula (I) in anhydrous crystalline Form 2 is characterized by an X-ray powder diffraction pattern which at least substantially includes the X-ray powder diffraction (XRPD) °2θ peaks at essentially the following positions: 8.3±0.1, 9.3±0.1, 10.2±0.1, 11.2±0.1, 13.6±0.1 degrees, which correspond respectively to d-spacing at 10.7, 9.5, 8.7, 7.9 and 6.5 Angstroms (Å).

In another embodiment, the crystalline form of 4-methylbenzenesulfonate salt of the compound of formula (I) is a solvate.

In another embodiment, the solvate crystalline form of 4-methylbenzenesulfonate salt of the compound of formula (I) is a hydrate.

In a further embodiment, the hydrate crystalline form of 4-methylbenzenesulfonate salt of the compound of formula (I) is hydrate 1.

Figure 5:
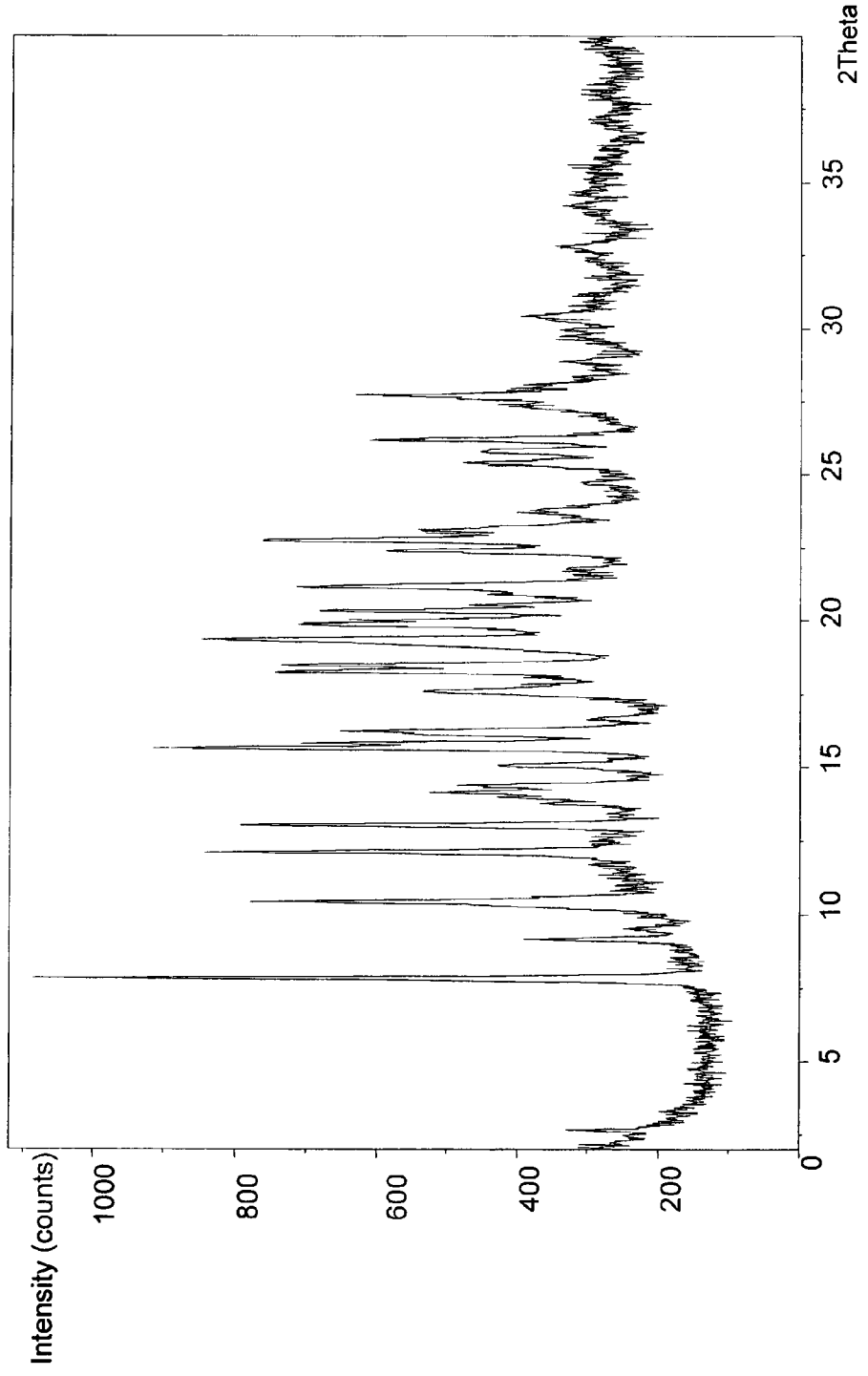
FIG. 5 depicts an X-ray powder diffraction (XRPD) pattern of 4-methylbenzenesulfonate salt of the compound of formula (I) in a hydrate crystalline form (hydrate 1), according to the present invention. The XRPD pattern is expressed in terms of 2 theta angles and obtained with a diffractometer using copper Kα X-radiation, according to the procedures described herein

In another embodiment, the crystalline hydrate 1 form of 4-methylbenzenesulfonate salt of the compound of formula (I) is characterized by substantially the same X-ray powder diffraction (XRPD) pattern as in FIG. 5, wherein the XRPD pattern is expressed in terms of 2 theta angles and obtained with a diffractometer equipped with a diffracted beam graphite monochromator using copper Kα X-radiation.

In another embodiment, the crystalline hydrate 1 form of 4-methylbenzenesulfonate salt of the compound of formula (I) is characterized by substantially the same differential scanning calorimetry (DSC) thermogram shown in FIG. 6.

In another embodiment, the crystalline hydrate 1 form of 4-methylbenzenesulfonate salt of the compound of formula (I) is characterized by an X-ray powder diffraction pattern which at least substantially includes the peaks of Table III.

TABLE III

| 2 theta angle (°)[1] | Å |
| --- | --- |
| 7.8 | 11.3 |
| 9.2 | 9.7 |
| 10.4 | 8.5 |
| 12.1 | 7.3 |
| 13.1 | 6.8 |
| 15.1 | 5.9 |
| 15.6 | 5.7 |
| 15.8 | 5.6 |
| 18.3 | 4.9 |
| 18.5 | 4.8 |
| 19.4 | 4.6 |
| 20.4 | 4.4 |
| 21.2 | 4.2 |
| 22.4 | 4.0 |
| 22.7 | 3.9 |
| 26.2 | 3.4 |

[1]Margin of error = approx. ±0.1 degrees.

In another embodiment, the crystalline hydrate 1 form of 4-methylbenzenesulfonate salt of the compound of formula (I) is characterized by an X-ray powder diffraction pattern which at least substantially includes the X-ray powder diffraction (XRPD) °2θ peaks at essentially the following positions: 7.8±0.1, 10.4±0.1, 12.1±0.1, 13.1±0.1, 18.3±0.1 degrees, which correspond respectively to d-spacing at 11.3, 8.5, 7.3, 6.8 and 4.9 Angstroms (Å).

In another aspect, the present invention provides pharmaceutical compositions comprising 4-methylbenzenesulfonate salt of the compound of formula (I) or a solvate thereof in a crystalline form.

Such pharmaceutical compositions may include one or more pharmaceutically acceptable carriers or diluents. Examples of suitable pharmaceutical compositions and methods for their preparation are described in a PCT Publication No. WO07/028654, the subject matter of which is incorporated herein by reference in its entirety. Conveniently, suitable pharmaceutical compositions can be prepared using conventional techniques, and when employed, carriers and diluents. Pharmaceutical compositions for oral administration, such as tablet and capsule formulations, are preferred.

Also provided in the present invention, is a method for treating in a mammal psychotic disorders, depression, mood disorders, anxiety, sleep disorders and substance-related disorders comprising administering to the mammal, an effective amount of 4-methylbenzenesulfonate salt of the compound of formula (I) or a solvate thereof in a crystalline form according to the present invention.

As another aspect, the present invention provides 4-methylbenzenesulfonate salt of the compound of formula (I) or a solvate thereof in a crystalline form according to the present invention for use in therapy.

As another aspect, the present invention provides the use of 4-methylbenzenesulfonate salt of the compound of formula (I) or a solvate thereof in a crystalline form according to the present invention in the preparation of a medicament for the treatment or prophylaxis of psychotic disorders, depression, mood disorders, anxiety, sleep disorders and substance-related disorders.

The compound of formula (I) can be prepared according to the method described in PCT Publication No. WO07/028654, the subject matter of which is incorporated herein by reference in their entirety.

Alternatively, the compound of formula (I) can be prepared according to the procedures described herein in the experimentals (from intermediates 1 to 7).

The 4-methylbenzenesulfonate salt of the compound of formula (I) may be prepared by contacting an appropriate stechiometric amount of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide free base with 4-methyl benzenesulfonic acid in a suitable solvent.

Suitable solvents for solubilising 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide free base include for example alcohols such as ethanol, ketones such as acetone, halogenated hydrocarbons such as dichloromethane, acetate esters such as ethyl acetate and ethers such as tetrahydrofuran.

The 4-methylbenzenesulfonate salt of the compound of formula (I) or a solvate thereof in a crystalline form may each be prepared by directly crystallising from a solvent in which the salt has limited solubility, or by triturating or otherwise crystallising a non-crystalline salt.

An improved yield of the salts may be obtained by the evaporation of some or all of the solvent or by crystallisation at elevated temperature followed by controlled cooling, for example in stages. Careful control of the precipitation temperature and seeding may be used to improve the reproducibility of the production process and the particle size distribution and form of the product. Certain factors influence which crystal form results.

These factors include, but are not limited to nucleation, seeding (both active and inadvertant) and solvent mediated effects. The solvent composition and solvent to product ratio is critical for the nucleation of the desired form. Typically seeding can influence the nucleation of the desired form from the solvent mixture.

Thus, for example, 4-methylbenzenesulfonate salt of the compound of formula (I) in anhydrous crystalline Form 1 may be obtained from a variety of organic solvents, such as toluene.

In an alternative process, anhydrous 4-methylbenzenesulfonate salt of the compound of formula (I) in crystalline Form 1 may be obtained by heating hydrate forms.

In a still further aspect of the invention there is provided a process for the preparation of 4-methylbenzenesulfonate salt of the compound of formula (I) in anhydrous crystalline Form 1 comprising reacting 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide free base with p-toluenesulfonic acid in a suitable solvent, for example, toluene and heating up to 80° C. until the material is dissolved and then cooling to 20° C. The 4-methylbenzenesulfonate salt of the compound of formula (I) in anhydrous crystalline Form 1 can be separated at this stage by filtration and then optionally dried.

In a further aspect of the invention there is provided a process for the preparation of 4-methylbenzenesulfonate salt of the compound of formula (I) in an anhydrous crystalline Form 2 comprising slurrying Form 1 or solvates thereof or a mixture thereof in a suitable solvent such as lower ketone e.g methyl isobutyl ketone or acetone, hydrocarbon solvent such as isooctane or heptane or a mixture thereof, heating at a temperature of about ambient to about the boiling point of the solvent, optionally adding the seeds, for a period of time to convert Form 1 into Form 2 and then cooling and isolating said anhydrous crystalline Form 2.

Solvates of 4-methylbenzenesulfonate salt of the compound of formula (I) may each be prepared by conventional means from a solution of 4-methylbenzenesulfonate salt. For example the hydrate 1 of the 4-methylbenzenesulfonate salt may be prepared by recrystallisation of the anhydrous Form 1 from water, a mixture of acetone and water or aqueous toluene.

4-methylbenzenesulfonate salt of the compound of formula (I) or a solvate thereof for use in the present invention may be used in combination with other therapeutic agents. Similarly, the pharmaceutical formulations of the present invention may include one or more additional therapeutic agents. The various therapeutic agents disclosed in PCT Publication no. WO07/028654, the subject matter of which is incorporated herein by reference in its entirety, that may be combined with the compound of formula (I) or salts thereof are similarly applicable to 4-methylbenzenesulfonate salt of the compound of formula (I) or a solvate thereof according to the present invention.

The invention thus provides in a further aspect the use of a combination comprising 4-methylbenzenesulfonate salt of the compound of formula (I) or a solvate thereof in a crystalline form with a further therapeutic agent to treat or prevent psychotic disorders.

When 4-methylbenzenesulfonate salt of the compound of formula (I) or a solvate thereof in a crystalline form is used in combination with other therapeutic agents, the compounds may be administered either sequentially or simultaneously by any convenient route.

When combined in the same formulation it will be appreciated that the two compounds must be stable and compatible with each other and with the other components of the formulation and may be formulated for administration. When formulated separately they may be provided in any convenient formulation, in such a manner as is known for such compounds in the art.

When 4-methylbenzenesulfonate salt of the compound of formula (I) or a solvate thereof in a crystalline form is used in combination with a second therapeutic agent, the dose of each compound may differ from that when the compounds are used alone. Appropriate doses will be readily appreciated by those skilled in the art.

4-methylbenzenesulfonate salt of the compound of formula (I) or a solvate thereof in a crystalline form and pharmaceutical compositions comprising the same are useful in therapy, particularly in the treatment or prophylaxis of psychotic disorders, depression, mood disorders, anxiety and sleep disorder in an animal, e.g. a mammal such as a human. The various therapeutic uses disclosed in PCT Publication no. WO07/028654, the subject matter of which is incorporated herein by reference in its entirety, are similarly applicable to 4-methylbenzenesulfonate salt of the compound of formula (I) or a solvate thereof in a crystalline form.

4-methylbenzenesulfonate salt of the compound of formula (I) or a solvate thereof in a crystalline form is especially useful for the treatment or prophylaxis of schizophrenia, anxiety, depression and sleep disorders and substance-related disorders.

The present invention also provides a method for the treatment or prophylaxis of psychotic disorders, depression, mood disorders, anxiety and sleep disorder in an animal, e.g. a mammal such as a human, which comprises administering to the animal an effective amount of 4-methylbenzenesulfonate salt of the compound of formula (I) or a solvate thereof in a crystalline form.

The foregoing method is particularly useful for the treatment or prophylaxis of schizophrenia, anxiety, depression and sleep disorders and substance-related disorders.

The present invention also provides the use of 4-methylbenzenesulfonate salt of the compound of formula (I) or a solvate thereof in a crystalline form in the preparation of a medicament for the treatment or prophylaxis of psychotic disorders, depression, mood disorders, anxiety and sleep disorder in an animal, e.g. a mammal such as a human, particularly for the treatment of schizophrenia, anxiety, depression, sleep disorders and substance-related disorders.

The following examples are intended for illustration only and are not intended to limit the scope of the invention in any way.

In the procedures that follow, after each starting material, reference to a description is typically provided. This is provided merely for assistance to the skilled chemist. The starting material may not necessarily have been prepared from the batch referred to.

In the Examples unless otherwise stated:

Proton Magnetic Resonance (NMR) spectra were recorded on Bruker instruments at 400 or 700 MHz, chemical shifts are reported in ppm (δ) using the residual solvent line as internal standard. Splitting patterns are designed as s, singlet; d, double; t, triple; q, quartet; m, multiplet; b, broad. Differential scanning calorimetry (DSC) was carried out on a TA Q1000 calorimeter, at a scan rate of 10° C. per minute. Sample size of between 1 and 2 mg weighed into an aluminium pan, a pan lid placed on top and lightly crimped without sealing the pan.

The X-Ray Powder Diffraction (XRPD) analysis shown in the FIGS. 1, 3 and 5 with a PANalytical X'-Pert Pro powder diffractometer equipped with an X'Celerator detector using copper Kα X-radiation. The acquisition conditions were: generator tension: 40 kV, generator current: 45 mA, start angle: 2.0° 2 theta, end angle: 40.0° 2 theta, step size: 0.0167° 2 theta, time per step: 31.75 seconds. The sample was prepared by mounting a few milligrams of sample on a silicon wafer (zero background) plate, resulting in a thin layer of powder.

2 Theta diffraction angles and corresponding d-spacing values account for positions of various peaks in the XRD pattern, d-spacing values are calculated with observed 2 theta angles and copper Kα1 wavelength using the Bragg equation. Slight variations in observed 2 theta angles and d-spacings are expected based on the specific diffractometer employed and the analyst's sample preparation technique. More variation is expected for the relative peak intensities. Large variations of relative peak intensities may be observed due to preferred orientation resulting from differences in crystal morphology. Variations in observed 2 theta angles and d-spacings may also be observed depending on the temperature at which the values are measured.

Identification of the exact crystal form of a compound should be based primarily on observed 2 theta angles or d-spacings.

The 20 or so most intense peaks plus low angle peaks have been included in the preceding Tables I-III.
Thermal Analysis.

Differential scanning calorimetry (DSC) was carried out on a TA Q1000 TA calorimeter. The sample was weighed into an aluminium pan, a pan lid placed on top and light crimped without sealing the pan. Scan rate of 10° C. per minute. Sample size of between 1 and 2 mg. When reporting DSC data, the onset or peak temperature of an event can be reported. In the current filling, onset temperatures are only reported. The onset temperature is the intersection of the leading event tangent with the baseline.

When the melt is combined with the degradation, the person skill in the art will appreciate that small variation in the onset melt temperature may be observed with different batches of the same material.

The following abbreviation are used in the text:
MIBK for Methyl isobutyl ketone, NMR for Nuclear Magnetic Resonance; ppm for parts per million; XRPD for X-ray powder diffraction; DSC for Differential scanning calorimetry; w/w for weight/weight; mL for milliliters; g for grams.

Intermediate 1

Methyl N-(phenylmethyl)-D-serinate

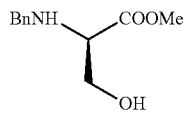

30.00 g of methyl-D-serinate 16.61 g sodium acetate and 300 mL tetrahydrofuran was loaded into the vessel at 20° C. 21.49 g (20.56 mL) benzaldehyde was added at 20° C. and the resulting mixture was cooled down to 0-5° C. 3.0 mL acetic acid (99-100%) was added and the reaction mixture was stirred for 1 h at 0-5° C.

89.91 g sodium tris-acetoxyborohydride was added portion-wise over 15 min. and the reaction mixture was stirred for 2-3 h at 0-5° C.

To the suspension was added at 0-5° C., 375 mL sat. sodium carbonate solution over 45 min. (gas evolution, pH adjusted to 8-9). The quenched mixture was warmed to 20-25° C. over 0.5 h. 300 mL water and 300 mL tert-butyl methyl ether were added at 20-25° C. and phases were separated. The organic layer was washed with 150 mL water and the combined aqueous layers were re-extracted with 150 mL tert-butyl methyl ether. The combined organic layers were washed with 90 mL water and the organic layer was concentrated to dryness at 35° C. under reduced pressure to afford the title compound 36.36 g. as a colourless oil.

¹H-NMR [ppm, CDCl₃]: 7.40-7.20, (m, 5H); 3.88-3.81, (m, 1H); 3.81-3.68, (m, 2H); 3.72, (s, 3H); 3.67-3.58, (m, 1H); 3.45-3.37, (m, 1H); 2.60, (bs, 2H).

Intermediate 2

(3R)-4-{[(1,1-dimethylethyl)oxy]carbonyl}-3-morpholinecarboxylic acid

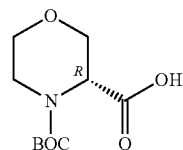

30.00 g of 4-{[(1,1-dimethylethyl)oxy]carbonyl}-3-morpholinecarboxylic acid (racemic mixture) and 300 mL isopropanol was loaded into the vessel at 20° C. 11.00 g (11.6 mL) of (S)-(−)-phenylethylamine was added at 20° C. The clear solution was heated to 80° C. and stirred for 10 min. at 80° C. The solution was cooled to 10-15° C. during 4 h. The suspension was stirred for 2 h at 10-15° C. then filtered and washed with 60 mL isopropanol. The filter cake was dried at 40° C. under reduced pressure to afford the diastereomeric salt as a white solid.

18.40 g of diastereomeric salt was transferred into the vessel and 92 mL water was loaded into the vessel at 20° C. and stirred for 15 min. 184 mL isopropyl acetate was added and cooled down to 0-5° C. 26 mL sodium hydrogensulphate (20% solution) was added dropwise during 10 min. to adjust the pH 3.0-3.5 at 0-5° C. The biphasic mixture was warmed to 20-25° C. and stirred for 30 min. Phases were separated, the aqueous layer was washed with 92 mL isopropyl acetate. The combined organic layers were concentrated to 74 mL at 45° C. under reduced pressure (white suspension obtained). 184 mL heptane was added and concentrated again to 74 mL at 45° C. under reduced pressure. 184 mL of heptane was added and the mixture was cooled down to 5-10° C.

The suspension was stirred for 10 min. at 5-10° C. then filtered over the nutsch and washed with 2× 36.8 mL heptane. The filter cake was dried at 45° C. under reduced pressure to afford the title compound as a white solid (10.13 g).

¹H-NMR [ppm, CDCl₃]: 11.56-11.15, (bs, 1H); 4.62, (d, 1H); 4.50-4.30 (dd, 1H); 4.00-3.83, (dd, 1H); 3.82-3.61 (m, 2H); 3.57-3.43, (m, 1H); 3.40-3.16, m (m, 1H); 1.50, (s, 9H).

Intermediate 3

(7R,9aR)-7-(hydroxymethyl)-8-(phenylmethyl) hexahydropyrazino[2,1-c][1,4]oxazine-6,9-dione

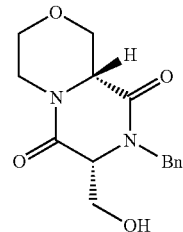

5.00 g of Intermediate 2 was suspended in 50 mL dichloromethane at 20° C. 6.22 g N-(3-dimethylaminopropyl)-N'-ethylcarbodiimide hydrochloride was added and the suspension was cooled to 0-5° C. 3.97 g of 1-hydroxybenzotriazole hydrate was added and the mixture was stirred for 45 min. at 2° C. 4.75 g of Intermediate 1 dissolved in 15 mL dichloromethane was added dropwise over 5 min. at 3° C. 6.15 g (8.14 mL) N,N-diisopropylethylamine was added to give a pale brown solution and the reaction mixture was stirred for 16 h at 0-5° C. Sat. ammonium chloride solution (40 mL) was added at 0-5° C. and the phases were separated. The aqueous layer was re-extracted with dichloromethane (50 mL) and the combined organic layers were washed successively with sat. sodium chloride solution (40 mL) and water (40 mL). The organic layer was treated with 27 mL 5-6N HCl in isopropanol at 20-25° C. The mixture was stirred for 3 h at 35-40° C. The reaction mixture was cooled down to 0-5° C. and 165 mL sat. sodium bicarbonate solution was added to afford a pH of 8. The phases were separated and the aqueous layer was re-extracted with 2×10 vol dichloromethane. The combined organic layers were concentrated at 50° C. under reduced pressure. 50 mL of methanol was added and the mixture was partially concentrated again at 50° C. A further 50 mL methanol was added. After solvent switch the mixture was stirred for 0.5 h at 20-25° C. The mixture was partially concentrated at 50° C. and 50 mL isopropanol was added. The added isopropanol was distilled off at 50° C. and a further 50 mL isopropanol was added furnishing a suspension (product suspension intermediate 3). The product suspension was cooled down to 0-5° C. and stirred for at least 1 h.

Filtration, washing with 10 mL isopropanol and drying at 45° C. of the filter cake afforded the title compound as a white solid. 2.81 g $^1$H-NMR [ppm, CDCl$_3$]: 7.42-7.15, (m, 5H); 5.34, (d, 1H); 4.47, (d, 1H); 4.36-4.19, (m, 2H); 4.07-3.93, (m, 2H); 3.93-3.82, (m, 3H); 3.67, (t, 1H); 3.47, (t, 1H); 3.40-3.26, (m, 1H), 2.88, (t, 1H).

Intermediate 4

[(7S,9aS)-8-(phenylmethyl)octahydropyrazino-[2,1-c][1,4]oxazin-7-yl]methanol

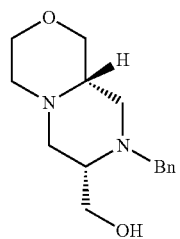

13.00 g of intermediate 3 was loaded into the vessel. 130 mL tetrahydrofuran was charged to afford a white suspension. The suspension was heated to 45-50° C. then 274 mL 1M borane-tetrahydrofuran solution was added in two portions (first 90 mL over at least 0.5 h) at 45-50° C. over at least 1 h (accumulation, gas evolution) affording a colourless solution. After complete addition, the feeding tank was washed with 13 mL tetrahydrofuran. The solution was stirred at 45-50° C. for 18 h. The reaction mixture was cooled down to 30° C. 32.5 mL methanol was added at 30° C. over 1.5 h (first 21 mL over at least 1 h (exothermic and strong gas evolution). 22 mL 6N hydrochloric acid was added at 30° C. over 0.5 h (gas evolution) affording a white suspension. The suspension was heated to 50° C. and stirred for 1 h after which the solvent was distilled off at 50° C. under reduced pressure. 195 mL water was added to the residue to give a thin white suspension. The suspension was heated to 40° C. and stirred for 1 h then extracted three times with 91 mL dichloromethane and the layers separated. 45.5 mL 3N sodium hydroxide solution was added to the aqueous layer over 15 min. affording a white suspension (pH has to be 7-8). The suspension was extracted three times with 130 mL dichloromethane and the combined organic layers were concentrated under reduced pressure at 40-45° C. to afford the title compound as a colourless oil. (Weight yield 97%)

$^1$H-NMR [ppm, CDCl$_3$]: 7.40-7.16, (m, 5H); 4.68 (bs, 1H); 4.16-4.06, (m, 1H); 3.90-3.71, (m, 4H); 3.68-3.54, (m, 2H); 3.20, (t, 1H); 2.88-2.61, (m, 5H); 2.52-2.39, (m, 2H); 2.29, (t, 1H).

Intermediate 5

(7S,9aS)-7-({[(1,1-dimethylethyl)(dimethyl)silyl]oxy}methyl)-8-(phenylmethyl)octahydropyrazino[2,1-c][1,4]oxazine

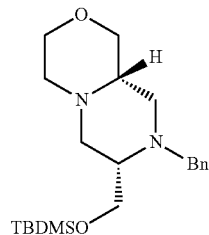

8.79 g imidazole was loaded into the vessel. A solution of intermediate 4 (30.80 g) in dichloromethane (308 mL) was charged to afford a colourless solution. A solution of 21.23 g tert-butyldimethylsilyl chloride in 61.6 mL dichloromethane was added at 0-5° C. over 10 min. affording a white suspension. The suspension was warmed to 20-25° C. and stirred for 2 h.

The suspension was filtered and washed with 61.6 mL dichloromethane to afford a colourless solution. To the solution was added 231 mL sat. sodium bicarbonate solution at 20-25° C. over 10 min. The biphasic mixture was stirred for 5 min. at 20° C. The phases were separated, the aqueous layer was extracted twice with 154 mL dichloromethane and the combined organic layers washed with water (2×231 ml), then concentrated under reduced pressure at 40° C. to afford the title compound as a colourless oil. (Weight yield 94%)

$^1$H-NMR: [ppm, CDCl$_3$]: 7.33-7.13; (m, 5H), 3.95, (t, 1H); 3.91-3.81, (m, 2H); 3.80-3.70, (m, 1H); 3.66-3.54, (m, 2H); 3.48, (d, 1H); 3.17-3.06, (m, 1H); 2.89-2.81, (m, 1H); 2.77, (d, 1H); 2.47, (d, 1H); 2.36-2.29, (m, 1H); 2.29-2.14, (m, 4H); 0.84, (s, 9H); −0.10-0.10, (2×s, 6H).

Intermediate 6

(7S,9aS)-7-({[(1,1-dimethylethyl)(dimethyl)silyl]-oxy}methyl)octahydropyrazino[2,1-c][1,4]oxazine

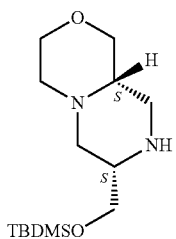

30.00 g GSK1497237A was loaded into the vessel. 360 mL ethanol was charged to afford a colourless solution. 3.0 g Pd/C 5% Type 458 (Paste) was added at 20-25° C. affording a black suspension. The suspension was heated to 50° C. and stirred for 2 h. under an atmosphere of hydrogen. The reaction mixture was cooled down to 20-25° C. and the suspension was filtered through an ethanol wet celite bed (90 g) and washed with 2× 60 mL ethanol. The filtrate was collected and concentrated under reduced pressure at 50° C. to afford the title compound as a yellow oil. (Weight yield 92.6%)

$^1$H-NMR [ppm, CDCl$_3$]: 3.95, (t, 1H); 3.78-3.69, (m, 1H); 3.63-3.50, (m, 3H); 3.13, (t, 1H); 2.92-2.83, (m, 1H); 2.58-2.32, (m, 5H); 2.29-2.14, (m, 2H); 1.98. (bs, 1H); 0.83, (s, 9H); −0.02-0.04, (2×s, 6H).

Intermediate 7

2-[3,5-bis(trifluoromethyl)phenyl]-N-{4-(4-fluoro-2-methylphenyl)-6-[(7S,9aS)-7-(hydroxymethyl) hexahydro-pyrazino[1,2-c][1,4]oxazin-8(1H)-yl]-3-pyridinyl}-N,2-dimethylpropanamide

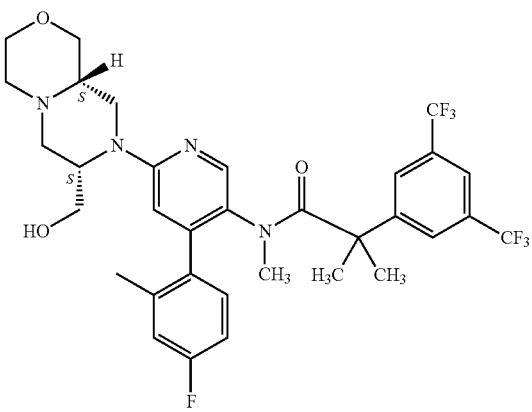

16.90 g of bis(trifluoromethyl)phenyl]-N-[6-chloro-4-(4-fluoro-2-methylphenyl)-3-pyridinyl]-N,2-dimethylpropana-mide (WO 2005/002577) 4.58 g sodium tert-butoxide and 2.10 g Bis-(tri-tert-butylphphosphine-palladium(0) catalyst was loaded into the vessel under nitrogen.

10.00 g intermediate 6 dissolved in 338 mL toluene was charged to afford a dark brown solution. The solution was heated to 80° C. and stirred for at least 16 h (thin suspension obtained).

The reaction mixture was cooled down to 20-25° C. and 16.90 g celite was added to give a brown suspension. The suspension was filtered over 16.90 g celite and washed with 33.8 mL toluene. 338 mL sat. sodium bicarbonate solution was added and the biphasic system was stirred for 5 min. at 20-25° C. After phase separation, the aqueous layer was extracted twice with 118 mL toluene. The combined organic layers were treated with 90 mL of a 10% aqueous cysteine solution and stirred for 1 h at 25° C. After phase separation the organic layer was treated again with 90 mL of a 10% cysteine-solution and stirred for a further 1 h at 25° C. After phase separation, the organic layer was washed with 85 mL half saturated sodium bicarbonate solution then solvent exchanged to dioxane.

The dioxane solution was cooled down to 10-15° C. 63.5 mL of 4M hydrogen chloride in dioxane was added at 10-15° C. over at least 10 min. The solution was warmed to 20-25° C. and stirred for 2 h.

Dioxane was concentrated down to 85 mL at 45° C. under reduced pressure. 85 mL water and 254 mL dichloromethane were added to the residue to give a thin suspension. The biphasic system was stirred for 5 min. at 20-25° C. The layers were separated and the organic phase was washed with 33.8 mL saturated sodium bicarbonate solution at 20-25° C. (pH adjusted to 7-8). The biphasic system was stirred for 5 min. at 20-25° C. and the organic layer separated and concentrated under reduced pressure at 50° C. to afford crude title compound as a pale brown solid.

8.00 g of the title compound (78.8% a/a HPLC) was dissolved in 16 mL ethyl acetate. The filter was loaded with 80 to 104 g silica gel and conditioned with ethyl acetate. The product solution was loaded on top of the column and chromatography was started using ethyl acetate as solvent. The product fractions were combined and partially concentrated at 45-50° C. under reduced pressure. To the mixture was added 2.64 g to 4.00 g silicycle (Si-Thiol, 1.2 mmol/g) at rt and stirred for 2 h. Filtration over 8.00 g celite and washing with 32 mL ethyl acetate gave the filtrate which was concentrated to dryness at 45° C. afford the title compound as a light brown solid. (Weight yield 72%)

$^1$H-NMR [ppm, CDCl$_3$]: 8.04-7.91, (m, 1H); 7.77, (s, 1H); 7.72-7.60, (m, 2H); 7.59-7.16, (m, 1H); 7.06-6.74, (m, 2H); 6.44, (s, 1H); 4.64-4.43, (m, 1H); 4.38-4.18, (m, 1H); 4.07-3.96, (m, 2H); 3.95-3.76, (m, 3H); 3.76-3.61, (m, 1H); 3.37-3.27, (m, 1H); 3.16-2.98, (m, 2H); 2.84-2.70, (m, 1H); 2.67-2.51, (m, 2H); 2.49-2.22, (m, 5H); 2.19-2.06, (m, 2H); 1.64-1.31, (m, 5H), OH broad and not observed Example 1

2-[3,5-bis(trifluoromethyl)phenyl]-N-{4-(4-fluoro-2-methylphenyl)-6-[(7S,9aS)-7-(hydroxymethyl) hexahydropyrazino[1,2-c][1,4]oxazin-8(1H)-yl]-3-pyridinyl}-N,2-dimethylpropanamide 4-methylbenzenesulfonate anhydrous crystalline Form 1

Preparation A 10.00 g intermediate 7 (97.8% a/a HPLC, purified by column) was loaded into the vessel. 100 mL toluene was charged to afford a red-brown solution and the solution was heated up to 80° C. 2.84 g p-TSA monohydrate dissolved in 150 mL water was added at 80° C. over at least 15 min. The reaction mixture was stirred for 1 h at 80° C. The reaction mixture was cooled down over 2-3 h to 20° C. and kept stirring at 20° C. for at least 4 h.

The suspension was filtered, washed twice with 20 mL toluene, filtered then dried under reduced pressure at 55-60° C. for at least 3 h. The title compound was isolated as an off-white solid. Weight yield 86%.

$^1$H-NMR [ppm, d$^6$-DMSO]: 9.99-9.40, (bs, 1H); 8.05, (s, 1H); 7.95, (s, 1H); 7.85-7.65, (m, 2H); 7.50, (d, 2H), 7.25-6.94, (m, 6H); 6.89-6.73, (m, 1H); 4.81-4.60, (m, 1H); 4.59-4.40, (m, 1H); 4.16-3.97, (m, 1H); 3.96-3.86, (m, 1H); 3.85-3.68, (m, 3H); 3.66-3.55, (m, 3H); 3.54-3.16, (m, 3H); 3.03-2.86, (m, 1H); 2.68-2.54, (m, 1H); 2.28, (s, 6H); 2.18-2.03, (m, 2H); 1.60-1.13, (2×s, 6H).

Preparation A is the use test batch that was prepared right before the large scale Preparation B here below.

An X-ray powder diffraction (XRPD) and Differential scanning calorimetry (DSC) were obtained and were consistent with anhydrous crystalline Form 1.

Preparation B 640 g intermediate 7 (96.8% a/a HPLC, purified by column) was charged to a reaction vessel. 10 volumes (6.4 L) toluene was charged to afford a red-brown solution and the solution was heated up to 80° C. 180 g (1.0 eq) p-toluenesulfonic acid monohydrate dissolved in 15 vol (9.6 L) water was added at 80° C. over at least 15 min. The reaction mixture was stirred for 1 h at 80° C. The reaction mixture was cooled down over about 3 h to 20° C. and kept stirring at 20° C. for at least 4 h. The suspension was filtered, washed with 5 vol (3.2 L) toluene, then dried under reduced pressure at 55-60° C. for at least 3 h. The title compound was isolated as a crystalline off-white solid (549 g).

$^1$H-NMR spectrum is consistent with that of the title compound obtained according to the preparation A described above.

X-Ray Powder Diffraction (XRPD)

The XRPD pattern is provided in FIG. 1.

Thermal Analysis.

DSC thermogram is depicted in FIG. 2.

Onset melt T=191.° C. by DSC

Example 2

2-[3,5-bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide 4-methylbenzenesulfonate anhydrous crystalline Form 2

Method A 50.0 g of [3,5-bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide 4-methylbenzenesulfonate anhydrous crystalline Form 1 was charged to a vessel along with 600 mL MIBK to afford a slight yellow solution. The mixture was warmed to 90° C. to ensure complete dissolution. The solution was then cooled to about 70° C. and seeded with 0.5 g of Form 2 suspended in 3 mL of MIBK and held at this temperature for at least 30 minutes. Heptanes (600 mL) were then added to the suspension over about 3 h. The suspension was then cooled to 20° C. over about 2.5 h and stirred for about 0.5 h at this temperature. The crystalline product was collected by filtration. The filter cake was washed with a mixture of 200 mL 1:1 MIBK/heptanes and then 400 mL heptanes. The filter cake was partially dried by suction and then under reduced pressure at ~55-60° C. to provide 41.5 g (83%) of the title compound.

X-Ray Powder Diffraction (XRPD)

The XRPD pattern is provided in FIG. 3.

Thermal Analysis.

DSC thermogram is depicted in FIG. 4.

Onset melt combined with degradation T=218.6° C. by DSC

Method B 3.2 g of 2-[3,5-bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide 4-methylbenzenesulfonate anhydrous crystalline Form 1 was charged to a vessel along with 8 volumes (26 mL) MIBK to afford a thin suspension. The mixture thickened in less than 30 minutes. The suspension was then temperature cycled between 20 and 40° C. over about three days. The title compound was collected by filtration.

An X-ray powder diffraction (XRPD) and Differential scanning calorimetry (DSC) were obtained and were consistent with anhydrous crystalline Form 2.

Example 3

2-[3,5-bis(trifluoromethyl)phenyl]-N-{4-(4-fluoro-2-methylphenyl)-6-[(7S,9aS)-7-(hydroxymethyl) hexahydropyrazino[2,1-c][1,4]oxazin-8(1H)-yl]-3-pyridinyl}-N,2-dimethylpropanamide 4-methylbenzenesulfonate crystalline hydrate 1

3.01 g of Example 1 preparation B was dispensed and made into a slurry in 23 ml of water. The slurry was prepared in a darkened fume cupboard. The cream slurry was transferred to a syn-10 block (with a magnetic stirrer inside) in a darkened container. The slurry was left to TC 0-40° C. at 500 rpm. Temperature cycling (TC) 0-40 involves rapidly heating to 40, holding for 1 hour, cool to zero over an hour and repeat cycle continuously. After two days TC 0-40° C. the slurry was removed. The slurry had thickened considerably and lightened in colour 2.815 g of solid was retrieved before drying overnight. The material was left to dry in the oven under vacuum at ambient temperature for one night; 2.805 g of the title compound was obtained.

Weight yield 93.1%

X-Ray Powder Diffraction (XRPD)

The XRPD pattern is provided in FIG. 5.

Thermal Analysis.

DSC thermogram is depicted in FIG. 6.

Onset dehydratation T=73.3.° C. by DSC

The invention claimed is:

1. 4-methylbenzenesulfonate salt of the compound of formula (I)

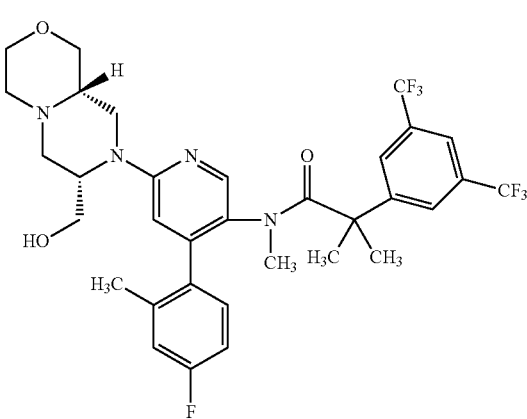

or a hydrate thereof in a crystalline form.

2. 4-methylbenzenesulfonate salt of the compound of formula (I) in a crystalline form as claimed in claim 1, wherein the crystalline form is anhydrous.

3. 4-methylbenzenesulfonate salt of the compound of formula (I) in a crystalline form as claimed in claim 1, wherein the crystalline form is hydrate.

4. 4-methylbenzenesulfonate salt of the compound of formula (I) in a crystalline form as claimed in claim 1, wherein the crystalline form is anhydrous crystalline Form 1 characterized by substantially the same X-ray powder diffraction (XRPD) pattern as in FIG. 1.

5. 4-methylbenzenesulfonate salt of the compound of formula (I) in a crystalline form as claimed in claim 1, wherein the crystalline form is anhydrous crystalline Form 2 characterized by substantially the same X-ray powder diffraction (XRPD) pattern as in FIG. 3.

6. 4-methylbenzenesulfonate salt of the compound of formula (I) in a crystalline form as claimed in claim 1, wherein the crystalline form is hydrate 1 characterized by substantially the same X-ray powder diffraction (XRPD) pattern as in FIG. 5.

7. A pharmaceutical composition comprising 4-methylbenzenesulfonate salt of the compound of formula (I) or a hydrate thereof in a crystalline form according to claim 1.

8. A pharmaceutical composition according to claim 7 further comprising one or more pharmaceutically acceptable carriers or diluents.

9. A method for the treatment of psychotic disorders, depression, mood disorders, anxiety, sleep disorders and alcohol dependence comprising administering to the mammal, an effective amount of 4-methylbenzenesulfonate salt of the compound of formula (I) or a hydrate thereof in a crystalline form according to claim 1.

* * * * *